United States Patent
Frigg et al.

(10) Patent No.: US 6,663,635 B2
(45) Date of Patent: Dec. 16, 2003

(54) BONE SCREW WITH TWO-PART SCREW HEAD

(75) Inventors: Robert Frigg, Bettlach (CH); Robert Ferus, Nennigkofen (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/036,464

(22) Filed: Jan. 7, 2002

(65) Prior Publication Data

US 2002/0161370 A1 Oct. 31, 2002

Related U.S. Application Data

(63) Continuation of application No. PCT/CH99/00303, filed on Jul. 7, 1999.

(51) Int. Cl.$^7$ .............................................. A61B 17/86
(52) U.S. Cl. ............................ 606/73; 606/61; 606/69
(58) Field of Search ............................ 606/53, 60, 61, 606/65, 66, 67, 68, 69, 70, 71, 72, 73, 75; 411/371–374, 378, 380, 383, 396, 397, 372.5, 372.6, 373, 377, 431, 910

(56) References Cited

U.S. PATENT DOCUMENTS

| | | | |
|---|---|---|---|
| 309,817 A | * | 12/1884 | Bartow |
| 824,983 A | * | 7/1906 | Farrington |
| 4,946,458 A | | 8/1990 | Harms et al. .................. 606/61 |
| 5,234,431 A | | 8/1993 | Keller ........................... 606/70 |
| 5,387,213 A | | 2/1995 | Breard et al. .................. 606/61 |
| 5,466,237 A | | 11/1995 | Byrd, III et al. ............... 606/61 |
| 5,569,247 A | | 10/1996 | Morrison ....................... 606/61 |
| 6,146,383 A | * | 11/2000 | Studer et al. |

FOREIGN PATENT DOCUMENTS

| | | |
|---|---|---|
| EP | 0 498 709 A1 | 8/1992 |
| EP | 0 507 162 A1 | 10/1992 |
| EP | 0 861 636 A2 | 9/1998 |

* cited by examiner

Primary Examiner—David O. Reip
(74) Attorney, Agent, or Firm—Pennie & Edmonds LLP

(57) ABSTRACT

The invention is related to a fastener and a bone fixation assembly for the internal fixation of vertebral bodies. The bone fastener includes a shank having a longitudinal axis, a head positioned adjacent the top end of the shank and having at least two portions separable in the axial direction. The head includes a bottom portion connected to the shank and a top portion connectable to the bottom portion. The bottom portion defines a socket situated coaxially to the longitudinal axis to accept a driver to rotate the fastener, and the top portion has an exterior with a convex design.

37 Claims, 3 Drawing Sheets

BONE SCREW WITH TWO-PART SCREW HEAD

CROSS-REFERENCE TO RELATED APPLICATIONS

This application is a continuation of the U.S. national stage designation of copending International Patent Application PCT/CH99/00303, filed Jul. 7, 1999, the entire content of which is expressly incorporated herein by reference thereto.

FIELD OF THE INVENTION

The present invention relates generally to osteosynthetic bone fixation devices, and in particular to a bone screw with a two-part screw head.

BACKGROUND OF THE INVENTION

Various devices for internal fixation of bone fragments in the human or animal body are known from the related art.

In the case of internal fixation of the spinal column or of parts of the spinal column, such devices often comprise pedicle screws which are anchored by means of threads into the pedicles of the individual vertebrae to be joined, and one or more longitudinal supports which extend in the direction of the spinal column and have to be connected securely to the pedicle screws. To achieve stable anchoring of the whole implant, the pedicle screws must on the one hand be screwed securely into the pedicles and, on the other hand, connected rigidly to the longitudinal supports.

The connection between the screw head of the pedicle screws and the longitudinal support is normally effected by means of clamp mechanisms which permit a stable connection, even at different angles of the pedicle screw in relation to the longitudinal support. The clamp connection may be releasable so that the whole implant can be removed again without leaving large tissue openings in the area of the spinal column. Secure connections between bone screws and plates or supports, which are common in other internal bone fixations, also may be used for internal fixation of the spine so that different angles of the bone screws relative to the plate or the support may be possible without adversely affecting the connections in terms of their stability.

For instance, one bone-anchoring screw and stabilizer rod connection for the internal fixation of vertebrae is known from U.S. Pat. No. 5,466,237 to Byrd ("Byrd"), which discloses a variable locking stabilizer, anchor seat, and screw. This known invention has a bone-anchoring screw with a screw head, which is designed as a segment of a sphere on its side facing the screw shank and is convex at its end. The spherical segment part of the screw is mounted in a bore of the anchoring element, this bore comprising a concave portion which tapers toward the screw shank so that a ball-joint-type connection is obtained between the bone screw and the anchoring element. This ball-joint-type connection is blocked by tightening a nut on the anchoring element, which nut presses against the longitudinal support which has been placed in the anchoring element and which consequently presses against the terminal convex part of the screw head and thus blocks the screw head in the anchoring element. However, in the case of a screw head which is convex at the end, there is a danger that the means for inserting a screwdriver in the screw head, for example a centrally arranged hexagon socket, will impair the contact surface between a longitudinal support, pressing on the screw head, and the screw head itself.

Despite this development, a need exists for a bone screw with a two-part screw head, where the bottom part of the screw head is securely connected to the screw shank and the top part of the screw head can be connected to the bottom part after implantation of the bone screw so that it is possible for the top surface of a convex screw head to be made smooth in the area of contact with another implant part, for example a longitudinal support, and a punctiform contact can be achieved between the top part of the screw head and the longitudinal support. A need also exists for a stable connection between a bone fastener and an anchoring element which permits different angles between the screw axis and anchoring element and which may permit a form fit with suitable material pairing.

SUMMARY OF THE INVENTION

The invention is related to a fastener and a bone fixation assembly for the internal fixation of vertebral bodies. The bone fastener includes a shank having a longitudinal axis, a head positioned adjacent the top end of the shank and having at least two portions separable in the axial direction. The head includes a bottom portion connected to the shank and a top portion connectable to the bottom portion. The bottom portion defines a socket situated coaxially to the longitudinal axis to accept a driver to rotate the fastener, and the top portion has an exterior with a convex design. The top portion at least partially covers the socket when the top portion is connected to the bottom portion.

The bone screw according to the invention comprises a screw shank to be anchored concentric to a longitudinal axis in a bone or bone part, and a likewise concentric, axially two-part screw head. The bottom part of the screw head toward the screw shank has a diameter which is greater than the diameter of the screw shank. The bottom part is designed as a segment of a sphere in the direction toward the screw shank. The top part of the screw head can be fitted on the bottom part or can be connected to the bottom part and screw shank by means of a press fit, a cone connection, a screw connection or a bayonet lock connection.

In the preferred embodiment of the bone screw according to the invention, the bottom part of the screw head and the screw shank are in one piece. In other embodiments, however, the bottom part can also be designed as a separate part, for example as a circular disk which can be pushed over a corresponding peg on the screw shank and which is clamped securely between the screw head and the screw shank when the top part of the screw head is secured.

The diameter of the bottom part of the screw head is preferably between 8 and 10 mm, while the diameter of the screw shank is preferably between 5 and 6 mm.

In a further embodiment of the bone screw according to the invention, the bottom part of the two-part screw head is designed as a circular disk. The thickness of such a circular-disk-shaped bottom part is preferably between 1 and 2 mm. The rim of such a bottom part is preferably stepped and has a lower edge for bearing on the wall of a bore with a curved surface. A linear contact is achieved in this way.

The top part of the screw head can be of convex design at the end, in particular spherical and semi spherical.

Depending on the embodiment, the bone screw according to the invention can be used for the fixation of bones or bone parts in an osteosynthesis fixation device and can serve, for example, for the fixation of bones or bone parts on a bone plate or for the fixation of vertebrae in a spinal column fixation device.

The device according to the invention for osteosynthetic bone fixation comprises at least one bone screw with a screw shank to be anchored in the bone or bone part and a screw head, and at least one fixation body which serves for stable fixation of the bones or bone parts. The fixation body has at least one bore for receiving the bone screw, this bore passing through the fixation body and comprising a concave portion tapering toward the end at the screw shank side. The bottom part of the screw head is in the shape of a segment of a sphere or in the shape of a circular disk, the diameter being dimensioned such that the bottom part, in the concave portion of the bore, can be made to bear on the wall of the bore at different angles between the longitudinal axis of the bone screw and the central axis of the bore. The configuration with a disk-shaped bottom part having a plane surface on the screw shank side, which surface bears on the concave wall of the bore upon tightening of the screw, permits a linear contact between the bone screw and the fixation body.

In one embodiment of the device according to the invention, this is used to connect a longitudinal support to the bone screw, designed as a pedicle screw, within a spinal column fixation system. The fixation body is designed as a receiving head which serves to connect the longitudinal support to the pedicle screw. Besides the through-bore passing through the receiving head in order to receive the pedicle screw, there is additionally a channel extending transverse to the central axis of the receiving head and open toward the screw head side in order to receive the longitudinal support. The device additionally comprises clamping means which can be connected to the receiving head in a releasable manner at the screw head end and serve for fixing the longitudinal support and the pedicle screw within the receiving head. The through-bore comprises a concave portion tapering toward its screw shank end, so that the screw head of the pedicle screw can be made to bear on the wall of the through-bore, in the concave portion of the through-bore, at different angles between the screw axis and the central axis of the bore.

In a further embodiment of the device according to the invention, the bottom part of the screw head has a diameter d, and the concave portion is of spherical design and has a diameter D, where D=d. However, with this design, with a circular-disk-shaped bottom part, only small angles of the screw axis relative to the central axis of the bore in the fixation body are possible, since otherwise the linear contact is obtained only on one part of the collar circumference. For greater angles in the case of circular-disk-shaped bottom parts, a design of the concave portion is suitable with a diameter D, where D>d. In this case, the ratio d:D can be chosen between 0.5 and 1.0, preferably between 0.85 and 0.95. In addition, the diameter of the screw head is chosen such that, if the bone screw is in an inclined position, the screw head does not bear on the wall of the bore and thereby restrict an inclined position of the bone screw.

In yet another embodiment of the device according to the invention, the concave portion is designed in the manner of a spherical segment, where the spherical segment has a radius X while the diameter of the concave portion is D, so that X>D. The ratio of D/2 to X is between 0.5 and 1.0, preferably between 0.85 and 0.95.

In a particular embodiment of the device according to the invention, the convex top part at the end of the screw head is of spherical or semispherical design. The center of the spherical top part can coincide with the sphere center of the spherical segment on the bottom part. In the case of the connection device between longitudinal support and pedicle screw, the advantage of this design lies in the fact that a longitudinal support clamped between screw head and clamping means presses on the screw head concentric to the central axis even if the pedicle screw is in an inclined position.

The convex screw head is axially in two parts, where the top part at the end of the screw head can be connected releaseably to the bottom part, which is made in one piece with the screw shank. Above all by means of the two-piece design, the means for inserting a screwdriver into the screw shank, for example a hexagon socket or internal thread, can be more easily provided. In addition, in the case of a central arrangement of, for example, a hexagon socket in the bottom part, the bearing between longitudinal support and screw head is not adversely affected by application of the top part after implantation of the bone screw.

In the case of a circular-disk-shaped bottom part, the rim of the bottom part is advantageously stepped, especially on the underside toward the screw shank, so that a lower edge is formed which is intended for linear contact with the wall of the concave portion.

The diameter D of the concave portion and the diameter d of the bottom part are advantageously between 8 and 10 mm. In the case of a circular-disk-shaped bottom part, the latter advantageously has a thickness of 1 to 2 mm.

The external diameter of the screw shank is advantageously 5 to 6 mm. The advantages that may be afforded by the invention include the design of the bone screw, the surface of the convex screw head in the area of contact with another implant part, for example the longitudinal support, is smooth and this contact zone is not impeded by means for receiving a screwdriver.

The advantages that may be afforded by the device according to the invention include the design of the bore for receiving a bone screw and the design of the bone screw with a screw head having a bottom part which is intended to bear in a concave portion of the bore so that, in the case of a circular-disk-shaped bottom part, a linear contact can be obtained which, upon fixation of the device, leads to a secure connection between bone screw and fixation body. In the case of a deformable bore wall, a form-fit connection between the bottom part and bore wall can also be achieved as a result of the linear contact.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
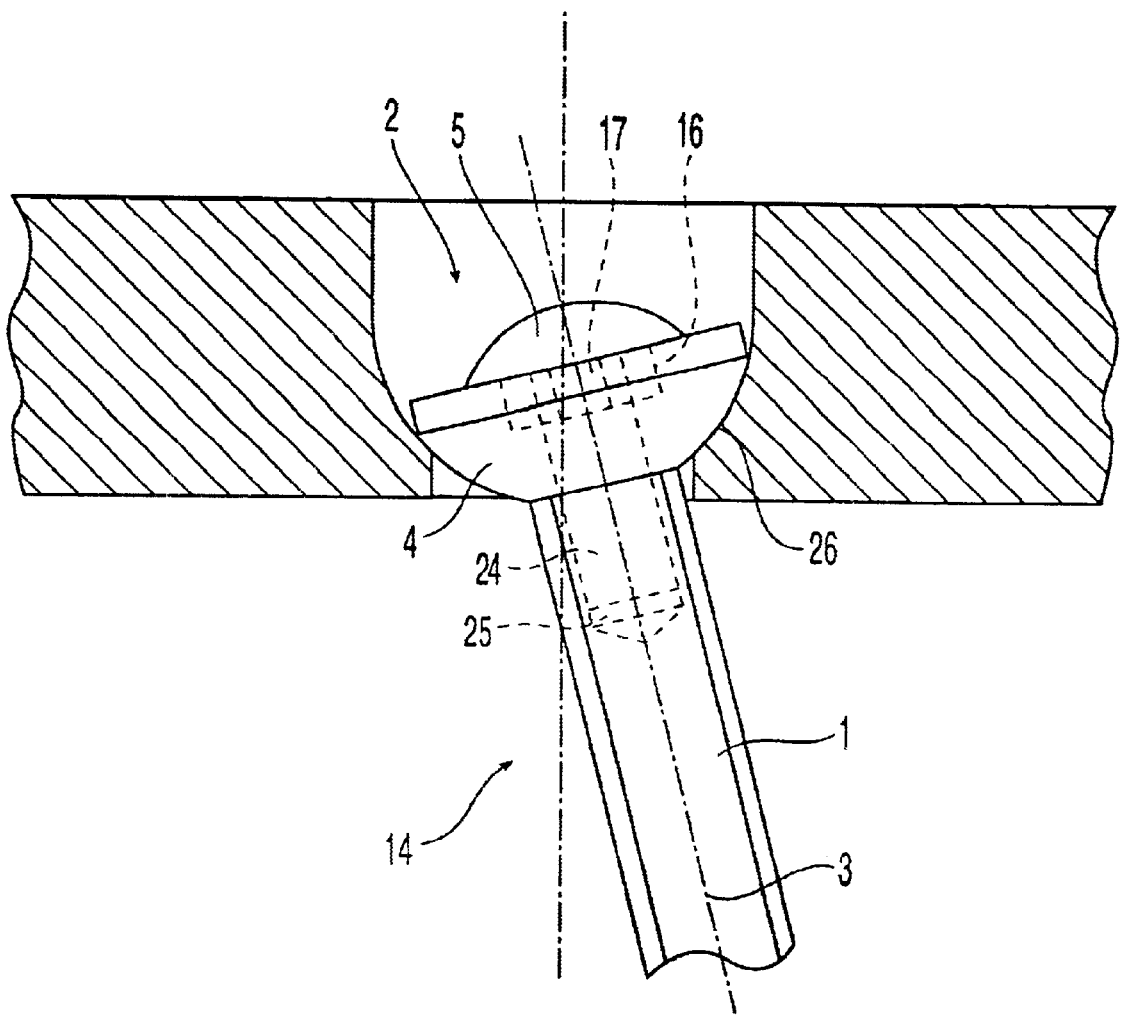
FIG. 1 is a cross-sectional view taken through an exemplary embodiment of the multi-part bone screw according to the invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Referring to FIG. 1, a two-part bone screw 14 is shown according to one embodiment of the invention. In this embodiment, the bone screw 14 comprises, concentric to the longitudinal axis 3 of the screw, a screw shank 1 and a screw head 2 which is in two parts separable in the axial direction and which consists of a bottom part 4 on the screw shank side and a top part 5 at the end. The screw shank 1 serves to anchor the bone screw in a bone or bone part. The bottom part 4 is of convex design toward the screw shank and has a bearing surface 26 in the form of a segment of a sphere. Bottom part 4 and screw shank 1 are in one piece. In this embodiment, the connection between top part 5 and screw shank/bottom part 4 is a press-fit connection. A peg 24 is arranged on the top part 5, concentric to the longitudinal axis 3 of the screw, and peg 24 can be introduced into a bore 25 in the screw shank 1, which bore is concentric to the longitudinal axis 3 of the screw. To turn the screw shank 1 into the bone or the bone part, a hexagon socket 16 is arranged on the bottom part 4, concentric to the longitudinal axis 3. The wrench width of the hexagon socket 16 can be selected such that the side surfaces 17 of the hexagon socket 16 do not touch the peg 24. The top part 5 is of a spherical design spaced axially at one end of the screw, so that the assembled screw head 2 is made convex at the end by the top part 5.

Figure 2:
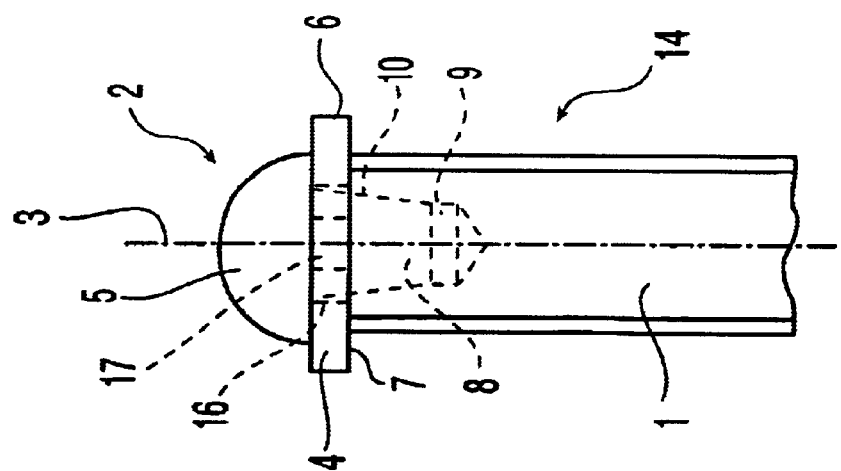
FIG. 2 is a cross-sectional view taken through another embodiment of the multi-part bone screw according to the invention.

Referring to FIG. 2, a further embodiment of the two-part bone screw 14 according to the invention is shown. The bone screw 14 comprises, concentric to the longitudinal axis 3 of the screw, a screw shank 1 and a screw head 2 which is in two parts separable in the axial direction and which consists of a bottom part 4 on the screw shank side and a top part 5 at the end. The screw shank 1 serves to anchor the bone screw in a bone or bone part. The bottom part 4 is stepped and has, toward the screw shank, a plane bearing surface 7 with a lower edge 6. Bottom part 4 and screw shank 1 are in one piece. In this embodiment, the connection between top part 5 and screw shank/bottom part 4 is a cone connection. Arranged on the top part 5, concentric to the longitudinal axis 3 of the screw, there is a conical peg 8 which can be secured in a bore 9 concentric to the longitudinal axis 3 of the screw, with an inner cone 10 in the screw shank 1. To turn the screw shank 1 into the bone or the bone part, a hexagon socket 16 is arranged on the bottom part 4, concentric to the longitudinal axis 3. The wrench width of the hexagon socket 16 can be selected such that the side surfaces 17 of the hexagon socket 16 do not touch the conical peg 8.

Figure 3:
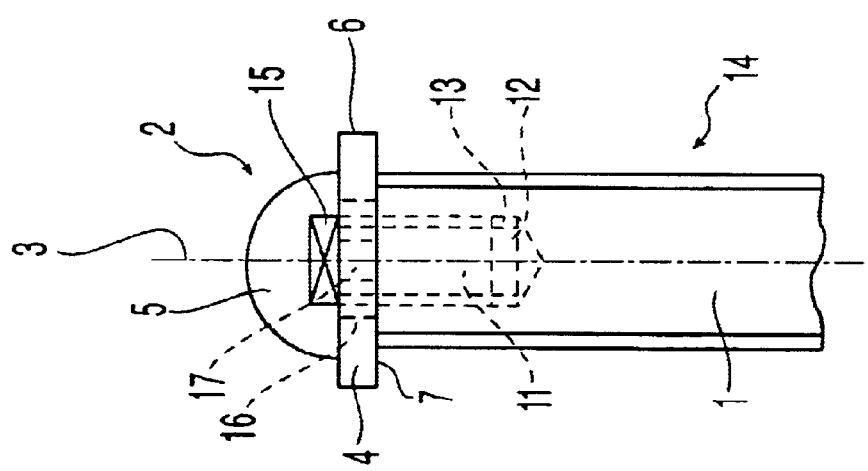
FIG. 3 is a cross-sectional view taken through a further embodiment of the multi-part bone screw according to the invention.

Referring to FIG. 3, another embodiment of the two-part bone screw 14 according to the invention is shown. The bone screw 14 of FIG. 3 differs from the embodiment shown in FIG. 2 only in that the connection between top part 5 and screw shank 1 is a screw connection. A threaded peg 11 is arranged on the top part 5, concentric to the longitudinal axis 3 of the screw, and the threaded peg 11 can be screwed into a bore 12, concentric to the longitudinal axis 3 of the screw. Bore 12 has an internal thread 13 on the screw shank 1. In this embodiment, bottom part 4 and screw shank 1 are in one piece. The hexagon socket 16 passes axially through the bottom part 4, while the bore 12 with the internal thread 13 begins only at that end of the screw shank 1 toward the bottom part and extends into the latter. Also arranged on the top part 5 there are two or more surfaces 15 oriented parallel to the longitudinal axis 3 of the screw and acting as external two edges for turning the screw shank 1 by means of a suitable screwdriver. In the alternative, it is also possible to have an external square or external hexagon, instead of the external two edges.

Figure 4:
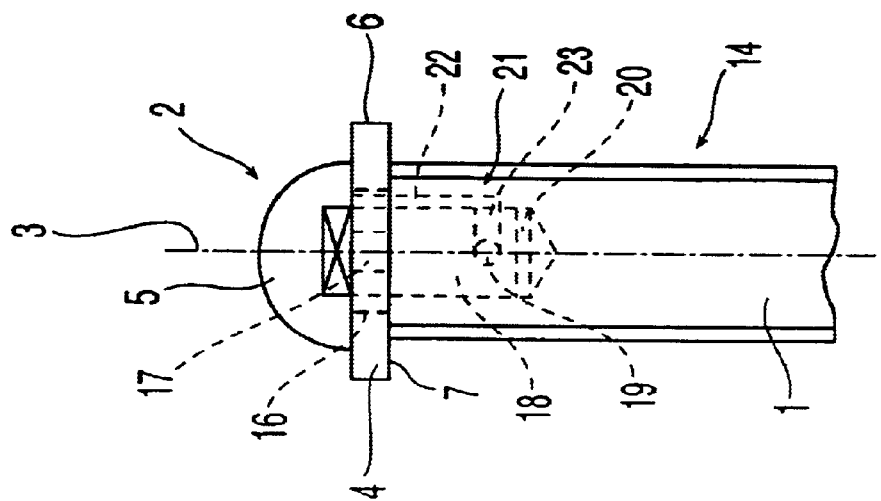
FIG. 4 is a cross-sectional view taken through another embodiment of the multi-part bone screw according to the invention.

Referring to FIG. 4, a further embodiment of the two-part bone screw 14 according to the invention is shown. The embodiment of FIG. 4 differs from the embodiment shown in FIG. 3 only in that the connection between top part 5 and screw shank 1 is a bayonet lock. A peg 18 is arranged on the top part 5, concentric to the longitudinal axis 3 of the screw. Peg 18 includes a radially protruding pin 19 which can be snapped into a bore 20, with groove 21, concentric to the longitudinal axis 3 of the screw. The groove 21 has a part 22 extending parallel to the longitudinal axis 3 of the screw and a part 23 extending peripherally into the bore 20.

Figure 5:
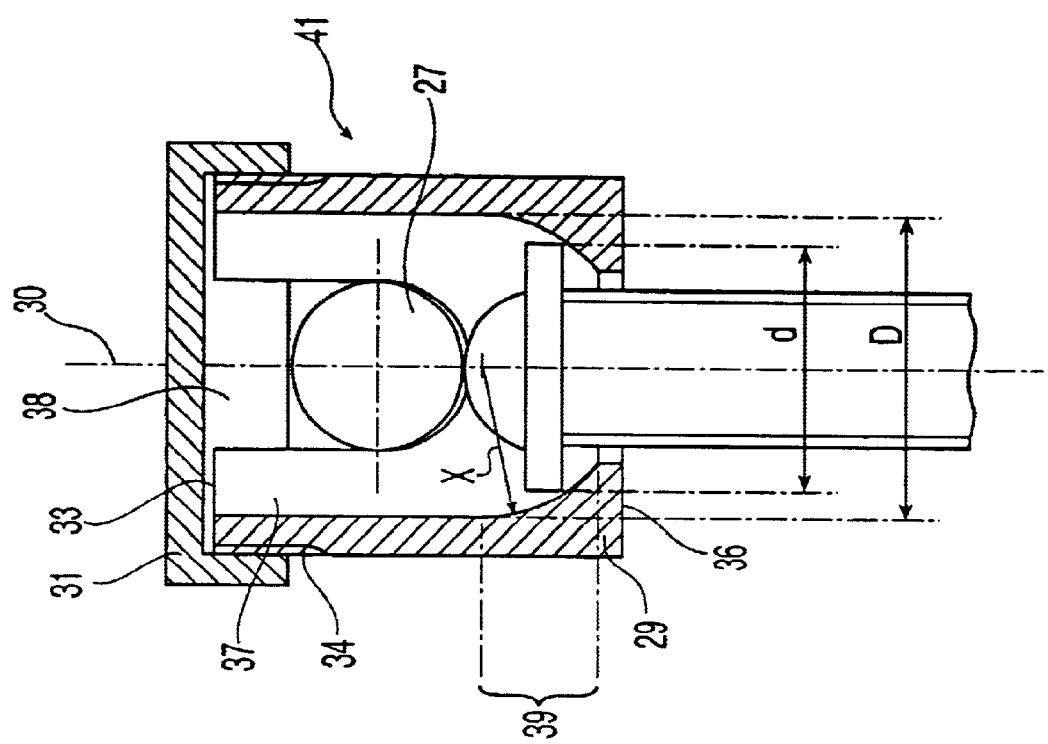
FIG. 5 is a cross-sectional view taken through part of an exemplary embodiment of a bone fixation assembly according to the invention parallel to a longitudinal support.
Figure 6:
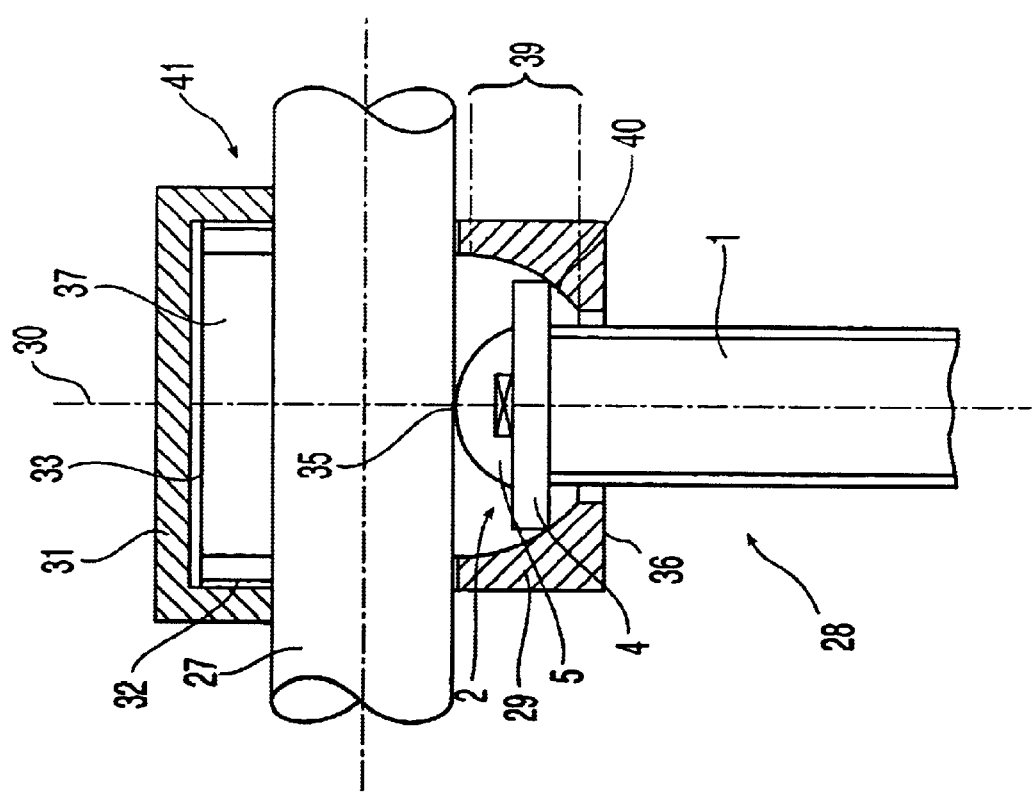
FIG. 6 is a cross-sectional view taken transverse to the longitudinal support through part of the bone fixation assembly shown in FIG. 5.

Referring to FIGS. 5 and 6, an embodiment of the bone fixation device according to the invention is shown which serves to connect a longitudinal support 27 to a pedicle screw 28 within a spinal column fixation system. This device comprises a pedicle screw 28 which has, concentric to its longitudinal axis 3, a screw shank 1 to be anchored in the bone, a screw head 2, a receiving head 29 with the central axis 30, which serves to connect a longitudinal support 27 to the pedicle screw 28, and clamping means 31. These clamping means 31 are generally in the form of a nut, and can be screwed by means of an internal thread 32 over an external thread 34 adjoining the upper side 33 of the receiving head 29 toward the screw head, and serve to fix the longitudinal support 27 and the pedicle screw 28 within the receiving head 29.

The screw head 2 is in two parts and has a bottom part 4 and a top part 5, their connection being designed in accordance with one of the embodiments shown in FIGS. 1 through 4 and described above. The top part 5 is designed as a segment of a sphere axially at one end, the zenith 35 of the sphere segment lying on the longitudinal axis 3 of the screw and forming the screw-head end of the pedicle screw 28.

The receiving head 29 has an upper side 33 toward the screw head, an underside 36 toward the screw shank, a through-bore 37 passing through the receiving head 29, coaxial to the central axis 30, for receiving the pedicle screw 28 and, additionally, a channel 38 extending transverse to the central axis 30 and open toward the upper side 33 in order to receive a longitudinal support 27. In this way, the longitudinal support 27 can be inserted from the upper side 33 into the open channel 38 and can be fixed therein in a releasable manner by the clamping means 31. The through-bore 37 comprises a concave portion 39 which tapers toward the underside 36 and which, in the embodiment of the device according to the invention shown here, is designed as a segment of a sphere.

The two-part screw head 2 has a concentric circular-disk-shaped bottom part 4 with a diameter d. The concave portion 39 is spherical with a radius of curvature X and, toward the upper side 33, opens into a cylindrical portion with the diameter D. In the embodiment of the device according to the invention shown here, the radius of curvature X corresponds to the radius of the cylindrical portion X=D/2. Likewise, in the embodiment shown here, the diameter d of the bottom part 4 is smaller than the diameter D of the cylindrical portion d<D. This dimensioning of the bottom part 4 and of the concave portion 39 ensures that the bottom part 4, in the concave portion 39 of the though-bore 37, can be made to bear on the wall 40 of the through-bore 37 at different angles between the longitudinal axis 3 of the screw and the central axis 30.

FIGS. 1–6 illustrate illustrate a bone screw 14; 28 for osteosynthetic bone fixation, with a screw shank 1 to be anchored concentric to the longitudinal axis 3 of the screw in a bone or bone part, and with a screw head 2. The bone screw 14; 28 is in more than one part axially, at least the screw head 2 being in two parts in the axial direction and comprising a bottom part 4 toward the screw shank and a top part 5 toward the end which can be connected to the bottom part 4 and/or to the screw shank 1. In a preferred embodiment the bottom part 4 and the screw shank 1 are in one piece.

In addition, the top part 5 of the bone screw 14; 28 can be connected in a releasable manner to the bottom part 4 and/or to the screw shank 1. In one variation, the top part 5 can be connected to the screw shank 1 or bottom part 4 by means of a cone connection. In another alternative, the top part 5 can be connected to the screw shank 1 or bottom part 4 by means of a screw connection. In another embodiment, the top part 5 can be connected to the screw shank 1 or bottom part 4 by means of a bayonet lock.

The bottom part 4 may be of convex design toward the screw shank. For example, in one variation the bottom part 4 of the bone screw 14; 28 is designed as a segment of a sphere toward the screw shank. In another embodiment, the bottom part 4 is designed as a circular disk. In addition, the rim of the bottom part 4 may be stepped and have a lower edge 6.

The top part 5 may be of convex design, with the zenith of the top part 5 intersecting the longitudinal axis 3 of the screw at one end. In one embodiment, the top part 22 is of spherical design. In another embodiment, the top part 5 is of semispherical design.

In addition, the diameter d of the bottom part 4 of the bone screw 14; 28 is preferably between 8 and 10 mm. Also, the bottom part (4) of the bone screw 14; 28 preferably has a thickness of 1 to 2 mm. Also, preferably the external diameter of the screw shank 1 is 5 to 6 mm. In another exemplary embodiment, the diameter d of the bottom part 4 is preferably between 4 and 6 mm. In another embodiment, the bottom part 4 preferably has a thickness of 0.5 to 1 mm. In another embodiment, the external diameter of the screw shank 1 is preferably 3 to 5 mm.

In use, the bone screw 14;28 is characterized in that it serves for the fixation of bones or bone parts in an osteosynthesis fixation device. In particular, the bone screw 14; 28, is particularly well-suited for the fixation of bones or bone parts on a bone plate. In one exemplary embodiment, the bone screw is a pedicle screw and serves for the fixation of vertebrae in a spinal column fixation device.

A device for osteosynthetic bone fixation according to one embodiment comprises at least one bone screw 14; 28 as described above, characterized in that it additionally comprises at least one plate-shaped, prismatic or cylindrical fixation body 41 which has at least one bore 37 with a central axis 30 for receiving the bone screw 14; 28, an underside 36 toward the screw shank, and an upper side 33 toward the screw head, with the bore 37 comprising a concave portion 39 tapering toward the underside 36, and the diameter d of the bottom part 4 being dimensioned such that the bottom part 4, in the concave portion 39 of the bore 37, can be made to bear on the wall 40 of the bore 37 at different angles between the longitudinal axis 3 of the screw and the central axis 30. In one embodiment, the bone screw 14; 28 used in the device is a pedicle screw 14; 28 with a convex screw head 2; and the fixation body 41 is a receiving head 29 with central axis 30, and additionally has a channel 38 extending transverse to the central axis 30 and open toward the upper side 33 in order to receive a longitudinal support 27; and the device additionally comprises in order to receive a longitudinal support 27; and the device additionally comprises clamping means 31 which can be connected to the receiving head 29 in a releasable manner from the direction of the upper side 33 and serve for fixing a longitudinal support 27 and the pedicle screw 14; 28 within the receiving head 29.

In one embodiment, the bottom part 4 has the diameter d, and the concave portion 39 is of spherical design and has the diameter D, where D=d. In another embodiment, the bottom part 4 has the diameter d, and the concave portion 39 is of spherical design and has the diameter D, where D>d. In one variation, the ratio d:D is between 0.5 and 1.0 and in another variation the ratio d:D is between 0.85 and 0.95.

In one embodiment, the concave portion 39 is designed as a segment of a sphere, where the spherical segment has a radius X, and X=D/2. In another embodiment, the ratio of D/2 to X is between 0.5 and 1.0. In another embodiment, the ratio of D/2 to X is between 0.85 and 0.95. In one embodiment, the diameter D of the concave portion 39 and the diameter d of the bottom part 4 are between 8 and 10 mm.

In one embodiment, the fixation body 41 is a bone plate with at least one through-bore for a bone screw 14.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone fixation device comprising:
    a bone fastener comprising:
        a shank having a longitudinal axis extending from a bottom end to a top end;
        a head positioned adjacent the top end of the shank and having at least two portions separable in the axial direction, the head comprising a bottom portion connected to the shank and a top portion attachable to the bottom portion;
        wherein the bottom portion defines a socket situated coaxially to the longitudinal axis to accept a driver to rotate the fastener; and
        wherein the top portion has an exterior with a convex design and the top portion at least partially covers the socket when the top portion is connected to the bottom portion;
    a bone plate comprising a plate bore configured and dimensioned to receive the bone fastener.

2. The bone fastener of claim 1, wherein the shank comprises a bone screw with threads suitable for the fixation of bones or bone parts in an osteosynthesis fixation device.

3. The bone fastener of claim 1, wherein the top portion is releasably connected to the bottom portion.

4. The bone fastener of claim 1, wherein the bottom portion and the shank are formed as an integral one-piece design.

5. The bone fastener of claim 1, wherein the top portion is attached to the bottom portion by means of a cone connection.

6. The bone fastener of claim 1, wherein the top portion is attached to the bottom portion by means of a screw connection.

7. The bone fastener of claim 1, wherein the bottom portion has an exterior surface adjacent the shank that is convex shaped.

8. The bone fastener of claim 1, wherein the bottom portion comprises a circular disk.

9. The bone fastener of claim 8, wherein the disk has a thickness in the axial direction of between 0.5 and 2 mm.

10. The bone fastener of claim 8, wherein the disk has a diameter "d" of between 8 and 10 mm.

11. The bone fastener of claim 1, wherein the bottom portion has an exterior surface adjacent the shank which is stepped in the axial direction.

12. The bone fastener of claim 1, wherein the top portion includes a zenith positioned to intersect the longitudinal axis of the fastener at one end.

13. The bone fastener of claim 1, wherein the top portion exterior is a segment of a sphere.

14. The bone fastener of claim 1, wherein the top portion exterior is semispherical.

15. The bone fastener of claim 1, wherein the shank is circular and has an external diameter of between 3 and 6 mm.

16. The bone fastener of claim 1, wherein the diameter d of the bottom portion is between 4 and 6 mm.

17. A bone fastener comprising:
a shank having a longitudinal axis extending from a bottom end to a top end;
a head positioned adjacent the top end of the shank and having at least two portions separable in the axial direction, the head comprising a bottom portion connected to the shank and a top portion attachable to the bottom portion;
wherein the bottom portion defines a socket situated coaxially to the longitudinal axis to accept a driver to rotate the fastener;
wherein the top portion has an exterior with a convex design and the top portion at least partially coven the socket when the top portion is connected to the bottom portion; and
wherein the top portion is attached to the bottom portion by means of a bayonet connection.

18. A bone fastener comprising:
a shank having a longitudinal axis extending from a bottom end to a top end;
a head positioned adjacent the top end of the shank and having at least two portions separable in the axial direction, the head comprising a bottom portion connected to the shank and a top portion attachable to the bottom portion;
wherein the bottom portion defines a socket situated coaxially to the longitudinal axis to accept a driver to rotate the fastener;
wherein the top portion has an exterior with a convex design and the top portion at least partially covers the socket when the top portion is connected to the bottom portion;
wherein the bottom portion has an exterior surface adjacent the shank that is convex shaped; and
wherein the bottom portion exterior surface includes a segment of a sphere adjacent the shank.

19. A bone fixation device comprising:
(1) at least one bone fastener comprising:
a shank having a longitudinal axis extending from a bottom end to a top end;
a head positioned adjacent the top end of the shank and having at least two portions separable in the axial direction, the head comprising a bottom portion connected to the shank and a top portion attachable to the bottom portion;
wherein the bottom portion defines a socket situated coaxially to the longitudinal axis to accept a driver to rotate the fastener; and
wherein the top portion has an exterior with a convex design and the top portion at least partially covers the socket when the top portion is connected to the bottom portion; and
(2) at least one fixation body having at least one bore with a central axis for receiving the bone fastener and defining an bore inner surface, wherein the bottom portion is dimensioned to contact the inner surface at different angles between the longitudinal axis of the shank and the central axis.

20. The device of claim 19, wherein the bone fastener is a pedicle screw, the fixation body is a receiving member with a channel extending transverse to the central axis to receive a longitudinal support therethrough; and
the device further comprises clamping means releasably connectable to the receiving member to fix the longitudinal support and pedicle screw within the receiving member.

21. The device of claim 19, wherein the fixation body is a bone plate.

22. A bone fastener comprising:
a threaded shank comprising an integrally formed, protruding bearing surface disposed proximate an end of the shank, a bore extending proximate a longitudinal axis of the shank, and a socket configured and dimensioned to receive a tool;
a head portion demountably attachable to the shank and comprising a partially spherical top part and a peg configured and dimensioned to be received in the bore;
wherein the bearing surface is partially spherical.

23. The bone fastener of claim 22, wherein the peg is integrally formed with the top part.

24. The bone fastener of claim 22, wherein the bearing surface comprises a convex shape.

25. The bone fastener of claim 22, wherein the peg comprises a conical shape.

26. The bone fastener of claim 22, wherein the peg comprises threading.

27. The bone fastener of claim 22, wherein the peg forms a bayonet lock when disposed in the bore.

28. The bone fastener of claim 22, wherein the socket is hexagonal.

29. The bone fastener of claim 22, wherein side surfaces of the socket are disposed remote from the peg when the peg is received in the bore.

30. The bone fastener of claim 22, wherein the protruding bearing surface is formed by a disk-shaped portion.

31. The bone fastener of claim 30, wherein the socket is disposed in the disk-shaped portion.

32. The bone fastener of claim 22, wherein the peg forms a press-fit in the bore.

33. A bone fixation device comprising:
(1) a first bone fastener comprising:
a threaded shank comprising an integrally formed, protruding bearing surface disposed proximate an end thereof, a bore extending proximate a longitudinal axis of the shank, and a socket configured and dimensioned to receive a tool; and a head portion demountably attachable to the shank and comprising a partially spherical top part and a peg configured and dimensioned to be received in the bore;

(2) a bone plate comprising a plate bore configured and dimensioned to receive the first bone fastener;

wherein the shank is positionable in a range of angles within the plate bore.

34. The bone fixation device of claim 33, wherein the plate bore comprises a concave portion and the bearing surface comprises a complementary convex surface for resting thereon.

35. The bone fixation device of claim 33, wherein the plate further comprises a portion for receiving a longitudinal support.

36. The bone fixation device of claim 35 wherein the longitudinal support bears against the head portion of the first bone fastener.

37. The bone fixation device of claim 35, further comprising a nut threadably associated with the portion receiving the longitudinal support.

* * * * *